United States Patent [19]

Staron

[11] 4,238,567

[45] Dec. 9, 1980

[54] PROCESS FOR PRODUCING FOOD PROTEINS FROM TRICHODERMA ALBUM

[75] Inventor: Thadée J. Staron, Noisy le Roi, France

[73] Assignee: Institut National de la Recherche Agronomique, Paris, France

[21] Appl. No.: 912,017

[22] Filed: Jun. 2, 1978

[30] Foreign Application Priority Data

Jun. 7, 1977 [FR] France ................................ 77 17449

[51] Int. Cl.³ ............................................. C12N 1/22
[52] U.S. Cl. .................................... 435/252; 426/18; 426/28; 426/44; 426/46; 426/48; 426/49; 426/61; 426/62; 426/615; 426/618; 426/622; 426/629; 426/634; 435/243; 435/945
[58] Field of Search .................. 426/7, 18, 28, 31, 42, 426/43, 44, 46, 48, 49, 55, 60, 61, 62, 615, 618, 622, 629, 634, 656; 195/81; 435/68, 251, 243, 252, 254, 272, 804, 945

[56] References Cited

U.S. PATENT DOCUMENTS

| | | | |
|---|---|---|---|
| 3,809,614 | 5/1974 | Forss et al. ............................ | 195/81 |
| 3,958,015 | 5/1976 | Gay ........................................ | 426/18 |
| 3,968,254 | 7/1976 | Rhodes et al. ........................ | 426/18 |
| 3,979,522 | 9/1976 | Scott ..................................... | 426/18 |
| 4,035,516 | 7/1977 | Jungrid ............................. | 426/44 X |
| 4,085,229 | 4/1978 | Staron .................................. | 426/46 |

FOREIGN PATENT DOCUMENTS

2303495 8/1973 Fed. Rep. of Germany ............ 195/81
880318 3/1943 France .

OTHER PUBLICATIONS

Microbiology Abstracts, Section A, vol. 12, 12A3242, 1977.
Chemical Abstracts, vol. 84, 57373n, 1976.
Chemical Abstracts, vol. 85, 112404w, 1976.
Chemical Abstracts, vol. 86, 176735h, 1976.

*Primary Examiner*—Robert J. Warden
*Attorney, Agent, or Firm*—Oblon, Fisher, Spivak, McClelland & Maier

[57] ABSTRACT

The process consists of cultivating, at a temperature below 28° C., the fungus Trichoderma Album in liquid nutrient media, the pH of said media being kept at a value comprised between about 3.7 and 4.8, the dissolved oxygen content being from about 6 to 10 mg/l. The cultivation is carried out with non-traumatizing, efficient stirring and under conditions such that multiplication is practically nil.

7 Claims, 4 Drawing Figures

PROCESS FOR PRODUCING FOOD PROTEINS FROM TRICHODERMA ALBUM

BACKGROUND OF THE INVENTION

1. Field of the Invention

The present invention relates to a process for producing food proteins of fungal origin or from multicellular organisms, in particular by the application of a novel multicellular organism. It relates also to the food proteins thus obtained. The invention also concerns a fermentation apparatus which is especially suitable for the application of the process according to the invention. Also it relates to a process for the mutation of micro-organisms and in particular of fungi.

2. Description of the Prior Art

Micro-organisms (bacteria, yeasts, fungi) play a part in the preparation of human and animal foodstuffs by acting through their enzymes and they are used for industrial production of organic molecules, of which many are common metabolites (ethanol, acetic acid, citric acid, glycerol, lysine, glutamic acid, ascorbic acid, etc. . . . ).

From the beginning of the era of Pasteur, commensal micro-organisms have been cultivated on various substrates (molasses, bagasse, lactoserum, bisulfite liquors, etc. . . . ) in order to enrich the byproducts and to product biomasses. The biomasses were especially utilized in animal foods as vitamin, mineral salt and protein supplements.

For conjunctural reasons, the development of these practices has long remained limited. The causes of this stagnation have been: irregularity in quality, difficulty in mastering the cultivation and maintenance of strains, appearance of cheaper sources of proteins and vitamins, industrial restructurization, following the discovery of fossil resources, which has accelerated agricultural development, etc. . . .

In the last twenty years, industrial production of biomasses has experienced a very distinct revival. The elements which have stimulated this return are principally: the progress of molecular biology, the discovery of micro-organisms consuming unconventional energy sources (for example paraffins), the need for the resorption of agroalimentary effluents in larger and larger volumes, growing needs for proteins, the appearance of new technologies attempting to reduce energy consumption, etc. . . .

Intense research into the cultivation of biomasses has developed since 1960. It has borne on alkane yeasts, bacteria oxidizing methanol, spirulines growing on carbonated media, mushrooms capable of metabolizing various types of effluents.

Nutritional tests carried out on numerous animal species have established the high nutritional value and inocuousness of biomasses thus obtained.

Micro-organisms capable of producing alimentary proteins are the bacteria and the fungi (yeasts and filamentous fungi); they must possess the following characteristics:

good specificity relative to the substrates,
short doubling time (20 min. to 5 hours);
high energy efficiency (100 g of carbohydrates = 25 to 32 g of proteins);
growth at required temperatures (from 20° C. to 50° C.);
growth at extreme pH's,
growth at low or high concentrations of substrates,
they must effect maximum exhaustion of the media (reduction of the C O D and of the B O D from 90 to 98%),
collecting and drying of the biomasse must be easy,
the protein content must be high (40–65%)
the nucleic acids and cellular wall contents must be low,
the germs used must not possess pathogenic ability (virulence and excretion of toxins) and they must not produce bacteriocins, nor release unpleasant flavors,
the protein efficiency coefficient (P.E.C.) of the biomass must be high.

It has been found, for the first time to the knowledge of Applicants, that a filamentous micro-organism could serve as a food.

Indeed, although the bacteria and the filamentous fungi are currently used in food technology and for the production of various metabolites, of vitamins, of aminoacids, of antibiotics, enzymes, etc. . . . , only the yeasts have been sufficiently widely cultivated to be consumed as foods. This capacity of yeasts to provide large amounts of biomasses is confirmed with the discovery of their property of growth on alkanes. Numerous works, reviews and treatises have been published on the production of the nutritional qualities of yeast-foods.

The filamentous micro-organism used in the process of the invention belongs to the Trichoderma genus.

It has been found also that such a filamentous micro-organism enables the value of certain protein substrates to be enhanced, notably protein substrates with a high protein content whose utilization is limited due to the fact that they contain for example toxic materials and/or materials giving them a certain bitterness.

The process according to the invention hence enables the production of food proteins arising from the action of this filamentous micro-organism on protein substrates. The invention relates also to the protein products thus obtained, these products being constituted by proteins of modified (purified, detoxified or bitterness-free) substrates possibly in admixture with proteins of filamentous micro-organism or soley proteins of filamentous micro-organisms.

The process for the production of food proteins comprises the steps of cultivating, under conditions which will be defined below, a polyphage filamentous micro-organism capable of metabolizing notably agricultural products and rejects of food industries or to purify, detoxify and eliminate the bitterness of protein substrates.

GENERAL DESCRIPTION OF THE INVENTION

The process according to the present invention comprises the step of:

(1) cultivating, at a temperature below 28 C the Trichoderma Album fungus in liquid nutrient media; the pH of said media being kept at a value comprised between about 3.7 and 4.8, the dissolved oxygen content being from about 6 to 10 mg/l, said culture being carried out with non-traumatizing efficient stirring and under conditions such that multiplication is practically nil.

The Trichoderma Album fungus applied in the process according to the present invention is a novel micro-organism which has been deposited in the National Collection of Micro-Organism Cultures of the Pasteur Institute in Paris under No. I-032 on 2 June 1977. This fungus as well as its process for production will be described in more detail in the description which follows.

The nutrient media which are suitable for the purposes of the present invention, that is to say on which Trichoderma Album develops, comprise liquid media containing protein nitrogen, amino nitrogen, or inorganic nitrogen (ammoniacal or nitric) which generally are put to waste. They are derived generally from agricultural products, byproducts and rejects of agroalimentary industries. These media can also be constituted by protein substrates whose value it is desired to enhance.

Among suitable agricultural products, may be mentioned for example, the flours: wheat, rye, corn, barley, oats, peas, etc. . . ; tubers and roots: potatoes, Jerusalem artichokes, manioc, sweet potatoes, beetroots, beetroot molasses and pulpes, carrots, swedes, etc. . . . ; fruit pulps and teguments: bananas, pineapples, oranges, apples, various marcs; fibrous products: bagasse, straws, wood. These media can be used as are or they may be previously pasteurized or sterilized.

Agroalimentary effluents and rejects which can be applied in the process according to the invention comprise notably bird droppings, liquid manure, household wastes, residual waters, effluents from preserving plants, protein plants, distillery vinasses, corn steep, diffusion waters from sugar plants, products derived from marine creatures, notably fish and crustacea (e.g. krill). These products are notably press liquors (soluble fish) and concentrates of soluble fish proteins.

By way of example, as protein substrates may be mentioned notably, beetroot pulp and soluble fish protein concentrates.

There may also be used mixtures of the above products by way of nutrient media.

When protein substrates which it is desired to enhance in value are applied, the Trichoderma Album fungus is cultivated under the previously indicated conditions, until the undesirable properties of the substrates are eliminated.

For example, when a soluble fish protein concentrate is used as a nutrient medium, which includes bitter substances, the process of the invention is applied until the protein substrate is devoid of bitterness. The protein substrate obtained includes obviously Trichoderma Album mycelium, which may or may not be removed by conventional separating means.

The soluble fish protein concentrates generally contain about 90% of protein which have a certain food value. Hence it is not necessary to convert these fish proteins into Trichoderma Album proteins; this is why in the case of the enhancement of the value of such substrates the fungus is allowed to act just for the time necessary to eliminate the bitterness; it will be easy for the one skilled in the art determine the time necessary to remove this bitterness. Tests have shown that generally it sufficed to leave the Trichoderma Album to develop in such media, under the above-indicated conditions, for about three to five hours.

Another protein substrate which can be used according to the invention is constituted by beetroot pulp. Beetroot pulp measures generally about 90% of water; this water is difficult to remove and by the prior art pressing methods there are generally obtained pulps of pressed beetroot measuring about 80% water. It has been found that by reacting Trichoderma Album with the beetroot pulp it is possible to obtain after pressing, pulps measuring only 50% of water. These products are useful for animal foods, notably that of bovine cattle.

In these cases, it is believed that Trichoderma Album eliminates, by hydrolytic action of its enzymes, the pectins contained in the beetroot pulp and which retain the water.

It may be advantageous, when a protein substrate of poor quality is used, to obtain a protein substrate having an improved protein value; this can be done according to the invention by allowing the Trichoderma Album to develop in the medium which has first been purified, detoxified or freed of its bitterness by the action of Trichoderma Album; it is then important to equilibrate the medium concerned by adding thereto carbohydrates and nitrogen. A protein product is then obtained constituted by the modified substrate and of a larger or smaller amount of proteins of the Trichoderma Album according to the degree of developement of the fungus reached at the time when the process of the invention is stopped.

When there are used as nutrient media, media without food value, the fungus is grown in this medium to extract the latter to the maximum. There are then obtained proteins of Trichoderma Album. It is then important to equilibrate the media.

The proportion of dry matter in the liquid nutrient media applied in the process according to the invention is conditioned by the exhaustion level of said media. If the media are completely exhausted, the ratio of dry matter can be high but a limiting factor exists which is the dissolved oxygen content, the latter having to be kept between 6 and 10 mg/l of medium. The exhaustion ratio of each medium is determined by weighting method, comparing the weight of mycelium obtained and the ratio of residual dry matter.

The nitrogen content (atomic N) of the nutrient media must be from about 4–5% of dry matter. In theory, 5 g of nitrogen are necessary to cause 100 g of carbohydrates to be consumed to produce about 32 g of proteins; it is hence necessary to adjust the nitrogen content of the media to a value in the neighborhood of this theoretical value. If the nitrogen content of the nutrient media is too high, carbohydrates are added thereto; on the other hand, if this content is too low nitrogen is added in a suitable form, notably in the form of ammonium sulfate or $NH_4$ nitrate and in a sufficient amount to have a nitrogen content of about 4–5 g for 100 g of dry matter.

Figure 1:
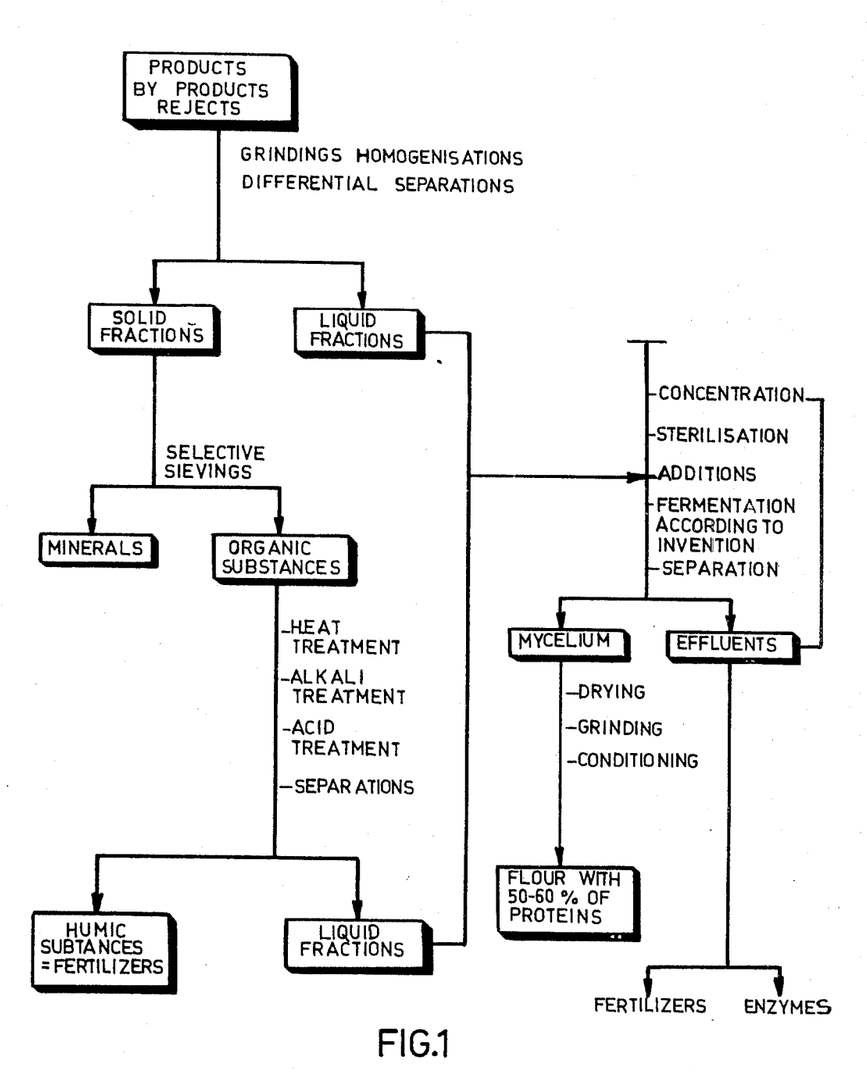
FIG. 1 shows as a flow sheet an embodiment of the process according to the invention for obtaining proteins of Trichoderma Album.

The liquid nutrient media may be obtained from agricultural products, byproducts and agroalimentary industry rejects, for example by the process shown in FIG. 1 which illustrates the production of Trichoderma Album proteins.

BRIEF DESCRIPTION OF THE DRAWINGS

In order that the invention may be more fully understood, an embodiment of the apparatus according to the invention and of the process according to the invention will be described in more detail with reference to the accompanying drawings given purely by way of illustrative and non-limiting example, and in which.

According to this process, the products, byproducts or rejects are subjected to one or several grindings, to one or several homogenizations, and differential separations. The resulting solid fractions are then treated by known conventional methods for the recovery of humic substances useful as fertilizers. The liquid fractions collected are assembled, concentrated, if necessary pasteurized or sterilized and their nitrogen content adjusted to a value of about 4–5% of dry matter before being subjected to the process according to the present invention. The mycelium recovered is then dried, and conditioned to give a protein flour containing 50–65% of proteins; the resulting liquid effluents are used as fertilizers or enzyme supplements.

The pH's of the culture media must be comprised between 3.7 and 4.8 and kept at a value comprised within this range throughout the culture. In fact, preliminary tests have shown that the exhaustion of the media rarely exceeds 50% in the case of a rapid fall in the dissolved oxygen and considerable variations of the pH. It is hence indispensable to maintain the pH within the above range in order to obtain optimization of the cultures. The pH is maintained automatically by dosing or proportioning devices which enable the addition to the nutrient medium of a base or an acid according to the value of the pH; it is possible to utilize, for example, sodium hydroxyde hydrochloric acid, sulfuric acid or any other suitable acid or base. In the same way, it is necessary for the dissolved oxygen content to be comprised between about 6 and 10 mg/l, preferably 8 mg/l.

The Trichoderma Album cultures are produced at a temperature below 28° C., preferably between 24° C. and 28° C. Trichoderma Album no longer develops at a temperature above 28° C. On the other hand, this microorganism grows at a temperature below 24° C. but at a very slow speed. It is hence advantageous to operate at a temperature comprised between 24° and 28° C.

The culture must be effected with non-traumatizing efficient stirring, that is to say with stirring which does not inhibit the growth of the micro-organism and in which the latter does not lyse.

The Trichoderma Album cultures can be produced in stirrers or in fermentation devices; it is a matter of respecting the above-defined operational conditions. It must be noted however that the growth of the microorganisms in submerged cultures, that is to say in fermentation devices, is generally much more rapid and the extraction of the media more complete in the case where the problems of stirring, of aeration and of multiplication are mastered.

The types of fermentation devices used to cultivate bacteria and yeasts are not very effective for developing filamentous fungi. The most difficult phenomena to master in applying the process of the invention are: stirring, aeration and multiplication.

Whereas yeasts and bacteria tolerate vigorous stirring, the growth of Trichoderma Album is severely inhibited above a rate of stirring of 150 rpm and the micro-organism lyses at 400 rpm. This phenomenon is an important limiting factor, since it is not possible to maintain the dissolved oxygen level at 4 mg/1 by stirring at less than 100 rpm.

Considerable aeration (1 to 3 l of air/l of medium/minute) cannot by itself maintain for more than three to six hours the level of dissolved oxygen at 5 mg/l. Besides, with large volumes of air, multiplication is impossible to master.

In the course of the fermentations, foams still pose problems. In the present case, antifoaming substances must be alimentary; consequently, antifoaming agents based on silicones are forbidden.

Vegetable oil mixtures and fatty acid salts have only given very average results.

It is hence necessary to modulate the stirring, the aeration and the amounts of antifoaming agent in order to effect a satisfactory compromise.

In order to obtain this satisfactory compromise, a novel fermentation apparatus has been perfected, which constitutes another aspect of the present invention.

The fermentation apparatus according to the present invention comprises, by way of essential elements: a fermentation device, oxygenation means, and antimultiplication means. It includes also regulating means for the temperature, the pH and the content of dissolved oxygen.

The fermentation device must include a slow system for mixing the mycelium and the culture medium; this mixing system may, for example, be constituted by a group of perforated trays on which the mycelium occurs, said trays being parallel and connected together by a system which permits them to be moved in the culture medium.

The oxygenation means must be suitable for oxygenating the culture medium; they may advantageously be constituted by a chamber centrifuge, which permits oxygenation outside of the fermentation device. Other apparatus for oxygenation outside of the fermentation device, such as centrifugal pumps, venturi, static mixers and oxygen columns may be found more suitable in the case of a change in the recycling levels used which depend on the substrates and their concentration.

The anti-multiplication means must permit the resorption of the foam formed, for example in the chamber centrifuge. These means must permit the formation of a liquid column overhanging with respect to the oxygenation means, completed if necessary by conventional chemical and mechanical means.

The device according to the invention may be used for the culture of bacteria, of yeasts, and of filamentous fungi. In the case of culture of filamentous fungi, it is necessary to provide de-clogging means; the latter may be constituted by an expansion vessel or by pneumatic means or continuously by an external filter, for example, strip-type or under vacuum. The separated microorganisms are in this case reinjected into the fermentation device by means of a volumetric pump or a conveyor belt. Although these means are not indispensable in the case of culture of the yeasts or bacteria, it is often advantageous to interpose an expansion vessel between the fermentation device and the oxygenation means.

DESCRIPTION OF THE PREFERRED EMBODIMENTS

Figure 2:
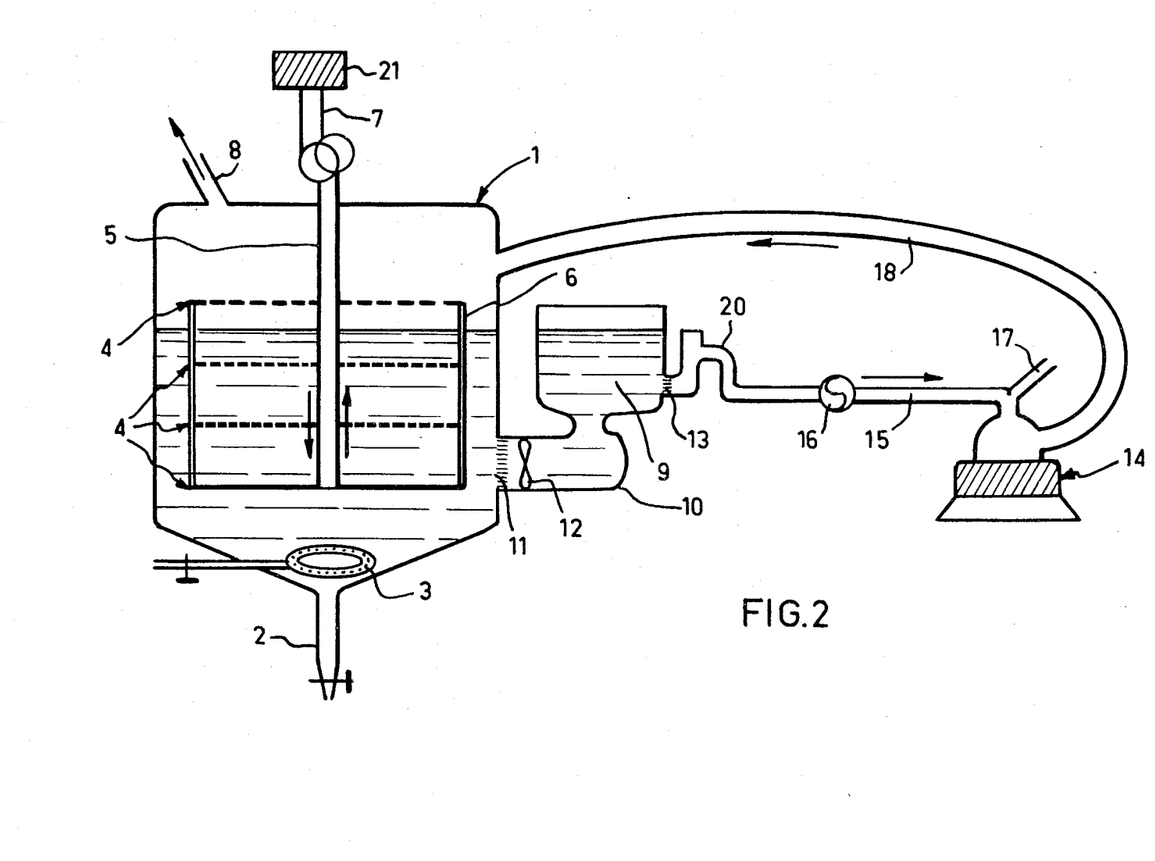
FIG. 2 shows diagrammatically a fermentation apparatus.
Figure 3:
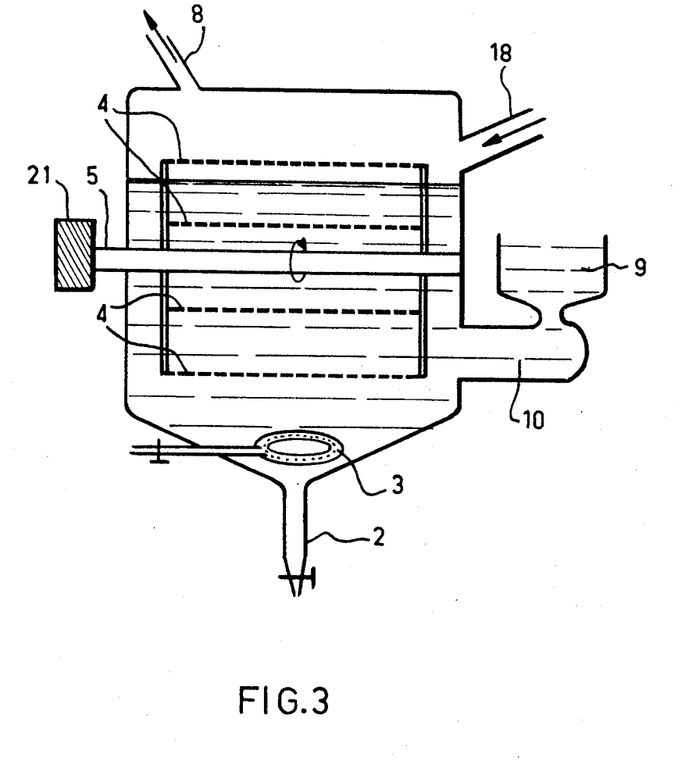
FIG. 3 shows another embodiment of fermentation apparatus.

An embodiment of the fermentation apparatus according to the invention suitable for the culture of filamentous fungi will now be described in detail with reference to FIG. 2, which is a diagrammatic view of this apparatus, and to FIG. 3, which is a particular embodiment with a modification.

The fermentation device of the apparatus according to the invention is constituted by a generally cylindrical vat 1, whose bottom is preferably in the shape of a truncated cone and is provided with a racking or drawing off pipe 2. This vat 1 includes aeration means 3 which enable the aeration of the culture media to be produced at the beginning of the culture of the filamentous fungi. It also includes a group of perforated trays 4 connected together by the support 5 and uprights 6. The support 5 is connected to an excentric system 7 driven by a motor 21 which permits the group of trays to be moved by actuating them with an up and down motion. The excentric system and the group of perforated trays constitute a sort of stirrer which permits the mycelium to rise above the liquid level. It is evident that this stirring system may be replaced by any other similar system. It is possible for example, to utilize the stirring system shown in FIG. 3. This stirring system, which constitutes a modification of the foregoing embodiment according to the invention, is constituted by a group of trays 4 connected to a horizontal axle 5 driven with a rotary movement, for example in the direction indicated by the arrow.

The fermentation vat 1 also includes a pipe 8 for the removal of gases (air and carbon dioxide). The fermentation device is connected to an expansion vessel 9 through a pipe 10 of large diameter. The pipe 10 is provided at its end connected with the fermentation device with a retention sieve 11 and with a closure valve 12. The expansion vessel 9 includes a retention sieve 13. It is connected to the chamber centrifuge 14 by a pipe 15 which includes if necessary a swan's neck 20 in the course of which is located a circulating pump 16 and an air inlet 17. The chamber centrifuge 14 is connected to the vat 1 through the pipe 18, which enters at the upper part of the vat 1.

Through the passage 17 it is possible inject air if necessary.

The pipe 18 must necessarily be of greater diameter than the inlet passage into the centrifuge and overhanging with respect to the centrifuge to permit the formation of a column of liquid in order to avoid multiplication; in this way, the foam formed is resorbed in the rising part of the pipe 18.

In the application of the process according to the invention in the fermentation apparatus defined above, the mixture of culture medium and micro-organism Trichoderma Album is produced slowly at the rate of about 15 to 30 movements per minute, by means of the system of perforated trays 4 which raise the mycelium above the liquid level.

During the three to four first hours of cultivation, aeration is effected through the bottom of the vat by aeration means 3; the aeration is thus effected at the beginning to avoid the passage of the filaments and growth in the expansion vessel; then, when the mycelium is in its exponential phase, the valve 12 is opened; the circulating pump 16 and the chamber centrifuge 14 in which the oxygenation is produced, are started; the ejection of the fluid occurs in surelevation in the passage of greater diameter 18 which permits the dissipation of the foam in the reconstituted liquid column. The reoxygenated medium pours into the vat of the fermentation device 1 at about 30 cm above the liquid level; the upper tray of the mixer pours the slight layer of foam into the medium. The two sieves 11 and 13 enables the nutrient medium to be filtered and the mycelium to be contained in the fermentation device. The flow rate is regulated as a function of the oxygen requirements. By means of this device, it is easy to maintain in the medium a suitable dissolved oxygen level (from 6 to 10 mg/l), and to ensure optimal growth of the micro-organism and maximum extraction of the culture media.

The apparatus according to the invention enables continuous cultivation; in this case, the sieves are partly open, the mycelium collected in the centrifuge is removed by washing or sluicing; a portion of the liquid removed is replaced by fresh nutrient medium.

The apparatus according to the invention, which enables efficient oxygenation of culture media and mastery of multiplication, is entirely suitable for cultures of bacteria and of yeasts. This fermentation apparatus according to the invention is hence a fermentation apparatus for micro-organisms in general (bacteria, yeasts, fungi).

In the case of cultures of bacteria and of yeasts, variable amounts of micro-organisms pass/into the centrifuge: at the beginning of culture, they are reinjected into the fermentation device by sluicing, then, in continuous culture, they are collected; the portion of the juice removed is replaced by fresh culture medium.

As has previously been indicated, the fermentations according to the process of the invention for obtaining proteins may be carried out continuously or batch-wise.

When the fermentations are carried out batch-wise, about 9/10 ths of the culture is withdrawn every 15 to 20 hours approximately and these 9/10ths of the culture are replaced by fresh adjusted and pasteurized medium. In numerous cases, recycling of the effluents is possible.

The protein product obtained according to the process for obtaining proteins may be advantageously collected or harvested according to the diagram below.

After drawing off, the harvest is recovered by filtration, for example, on a filter press or any other suitable filtration apparatus. After filtration, the culture is pressed to form a mycelian cake containing 30 to 50% by weight of dry matter. This mycelian cake is then dried, if necessary ground and conditioned for its preservation or its transport.

The drying of the protein product by freeze-drying, spray drying, fluidization or on a drying roller ("Hatmaker" type), band dryer or pneumatic dryer is very rapid. These drying processes enable the production of a food of exceptional quality leaving no viable cell.

On the other hand, static drying processes alter the nutritional value of the product. In fact, plasmolysis releases amino and simple glucidic structures which react by the "Maillard" reaction. Static drying processes are hence to be avoided.

At the outlet of the filter press, the protein product which contains notably Trichoderma Album mycelium possesses a well-individualized filamentous structure. On drying, the structure becomes very friable and breaks up spontaneously. When the protein product is constituted only by proteins of dry and ground mycelium, it is in the form of a white powder, of a density which varies between 0.6 and 0.9. This powder, non-multiplying, is onctuous, very easily wettable, odorless and tasteless. Certain culture media may however confer on it specific flavors.

Microscopically, no mycelium structure is observable. Only debris of various shapes are seen whose dimensions vary between 5 and 50μ.

The proteins of the Trichoderma Album obtained according to the process of the present invention are in the form of powder containing 50 to 65% of protein.

The percentage compositions and amino acid compositions of the mycelium of Trichoderma Album obtained according to the process of the invention and dried are given in Tables I and II below.

In table II are indicated the compositions of other proteins products obtained by conventional processes.

TABLE I
PERCENTAGE COMPOSITION OF TRICHODERMA ALBUM DRY MYCELIUM
(% by weight)

| | |
|---|---|
| Proteins (N × 6.25) | 55 to 63 |
| Non-protein nitrogen | 3 to 5 |
| Fats | 6 to 12 |
| Insoluble sugars | 8 to 10 |
| Soluble sugars | 7 to 10 |
| Nucleic acids | 4 to 6 |
| Ashes | 6 to 9 |
| Water | 3 to 5 |

As previously indicated, the Trichoderma Album species applied in the process of the invention is a novel species of filamentous fungi which has been selected in the Laboratories of the "Institut National de la Recherche Agronomique". The process of selecting the strain, which will be described below, also forms part of the scope of the invention. It can be applied with bateria, streptomyces and other fungi, notably *phycomycetes* (Rhizopus); *basidiomycetes* (Ustilago, Corticium, Fomes, Taphrina, Sclerotinia, Rhabdocline, Phacidiella, Epichloe, Nectria, Ophiobolus, Endothia); *adelomycetes* (Phoma,Ascochyta, Septoria, Collectotrichum,Gloeosporium,Monilia,Sterigmatocystis, Gliocladium,Geotrichum,Acrostalagmus, Trichoderma, Botrytis, Cephalosporium,Verticilium,Trichothecium, Aspergillus, Penicillium,Fusarium, Cladosporium, Pullularia, Torula, Thielaviopsis, Alternaria, Cercospora, Sporodesmium, Helminthosporium, Epicoccum, Graphium).

Some indications will first be given on the taxonomy and biology of fungi.

The fungi belong to the world of cryptogamous, eucaryotic, thallophytic, non-chlorophyllic vegetables.

More than 100,00 species of fungi are known; they are characterized by a very large multiplicity of forms, which range from the individualized cell (yeasts) to the complex organization of carpophores (cepes). There are considerable differences in size, appearance, structure, metabolic activities and mode of life.

Saprophytic fungi, pathogenic fungi, symbiotic fungi, and mycorhizian fungi are to be distinguished from each other.

In the micro-organisms, there are to be cytologically distinguished, a nucleus, mitochondria, vacuoles, lipid globules, and glycogen. The cell walls are constituted by cellulose, pectin, callose, chitin. The fungal protoplasm is endowed with motility, it can move from the central portion, which is vacuolized, towards the periphery.

TABLE II
COMPOSITION OF TRICHODERMA ALBUM
compared with other protein materials,
in percent per 16 g of N

| | Lactic casein | Soya cake | Sesame cake | "New Land" lupin flour | Paris Mushrooms | Trichoderma album dried on "Hatmaker" | Freeze-dried Trichoderma album | Plasmolysed water soluble Trichoderma album fraction | Plasmolysed water insoluble Trichoderma album fraction | Trichoderma album free amino acids |
|---|---|---|---|---|---|---|---|---|---|---|
| LYS | 8.2 | 6.4 | 2.8 | 5.3 | 6.9 | 8.3 | 8.3 | 10.4 | 5.9 | 7.1 |
| HIS | 3.7 | 3.2 | 3.1 | 2.4 | 1.7 | 2.2 | 2.6 | 2.4 | 2.3 | 0.9 |
| ARG | 4.4 | 7.7 | 14.2 | 12.0 | 4.9 | 5.6 | 5.8 | 6.4 | 5.6 | 4.2 |
| ASP | 6.7 | 11.4 | 8.1 | 10.4 | 9.5 | 10.0 | 9.4 | 10.2 | 10.8 | 10.9 |
| THR | 4.1 | 4.0 | 3.9 | 3.3 | 5.0 | 5.7 | 4.8 | 5.4 | 5.9 | 2.5 |
| SER | 4.9 | 5.1 | 4.6 | 3.9 | 4.7 | 5.2 | 5.3 | 5.7 | 5.4 | 8.1 |
| GLU | 20.3 | 18.5 | 19.7 | 24.1 | 24.7 | 13.6 | 16.0 | 12.0 | 13.8 | 11.5 |
| PRO | 10.6 | 5.3 | 3.5 | 4.5 | 6.1 | 5.4 | 5.5 | 5.2 | 5.1 | 3.2 |
| GLY | 1.6 | 4.0 | 4.4 | 3.3 | 4.2 | 5.2 | 4.2 | 6.0 | 5.2 | 2.2 |
| ALA | 2.6 | 4.2 | 4.4 | 3.2 | 7.9 | 6.5 | 6.3 | 7.1 | 6.3 | 8.7 |
| CYS-MET | 3.1 | 3.9 | 6.8 | 2.0 | 2.0 | 3.2 | 3.9 | 2.8 | 4.0 | 2.5 |
| VAL | 5.9 | 4.8 | 4.5 | 4.0 | 5.7 | 5.9 | 5.8 | 6.0 | 6.3 | 6.8 |
| ILE | 5.1 | 5.2 | 4.1 | 4.8 | 4.6 | 5.6 | 6.1 | 4.7 | 5.4 | 6.5 |
| LEU | 8.6 | 7.9 | 7.4 | 8.2 | 6.4 | 8.4 | 8.1 | 8.1 | 9.0 | 12.3 |
| TYR | 5.5 | 4.2 | 3.8 | 4.1 | 1.8 | 4.1 | 3.4 | 3.4 | 3.7 | 7.3 |
| PHE | 4.8 | 5.7 | 4.7 | 4.3 | 3.8 | 4.9 | 4.3 | 4.1 | 5.0 | 7.1 |
| PROT. MAT. in % M.S. | 91.4 | 52.6 | 53.9 | 34.8 | 40.5 | 56.7 | 63 | 75.0 | 45.0 | 4 |

Protein products constituted by a mixture of proteins of the substrate and of mycelium have a protein content which varies according to the starting substrate and the amount of mycelium.

The thallus builds reproducing elements (the spores), of sometimes very simple genesis:fragmentation (arthrospores) or budding (in the yeasts).

The spores can also be developed by very differentiated fructifying organs such as the cap of agarics or the perithecium of the pyrenomycetes.

The spores, whose formation involves the prior fusion of two compatible nuclei, followed by reductional division, ensure sexual or perfect reproduction.

The classification of fungi is based on the nature of the vegetative thallus, which may be:

(1) plasmodial in the myxomycetes,
(2) cellular or filamentous in the eumycetes.

In this second group, there are to be distinguished:

(a) The lower fungi (siphomycetes or phycomycetes) in which there is only one multinuclear generating filamentous cell. The filaments extend and branch without becoming partitioned and generally without being anastomosed. The cytoplasmic mass and the nuclei flow freely inside tubular walls.

The phycomycetes reproduce by enkystic eggs (oospores, zygospores) formed on the mycelium following conjugation between free gametes or between more or less differentiated filamentous sexual organs.

(b) The higher fungi or septomycetes (ascomycetes, hemiascomycetes, basidiomycetes, and imperfect fungi).

These fungi possess a mycelium constituted by microscopic filaments (the hyphae). The branched hyphae, juxtaposed, anastomosed, but never organized into tissues, are divided into mono- and multi-nuclear segments, by transverse partitions. These diaphragms, often incompletely closed, permit circulation of the protoplasm and of the nuclei from one cell to another. Anastomoses are frequent between hyphae of one species or a related species, which facilitates heterocaryosis. Heterocaryosis consists of the union in a same mycelium of nuclei carrying different genetic potentialities either because they result from mutations, or because they arise from different organisms.

The higher fungi generally produce their sexed spores in or on localized fructification members. The differentiation of their sexual elements is generally weak and fecundation tends to be manifested simply by the conjugation of related nuclei in non-specialized filaments; it leads to the formation of ascospores contained in asci or of basidiospores produced on basidia. In imperfect fungi, the reproduction is asexual, doubtless for lack of a compatible partner; multiplication is done by conidia.

The word of fungi is less extensive than that of plants. However, the biological characters of these microorganisms confer on them an astonishing plasticity and it has been observed that very numerous individuals contain genetic potentialities of a new breed or species. In these individuals, it has been found that it is possible to subtract the drawbacks and extract interesting characters, exploitable in numerous fields, notably for the production of alimentary biomasses.

The process of selection of advantageous characters of a micro-organism according to the invention comprises, in its most general aspect, the steps of cultivating a wild strain on selective culture media, incubating the cultures under specific conditions of temperature and lighting, proceeding with microisolations and mixing the improved strains in the presence, or not, of acridine organe, with reisolation of the white hyphae.

The selective culture media applied in the process of the invention are selected according to the troublesome criteria of the wild strain that it is desired to cause to disappear.

In its most detailed aspect, the process according to the present invention comprises the steps of:

(1) inoculating the selective media chosen with a wild strain, (2) incubating each culture under the following conditions, (a) at 27° C. for one day,
(b) at 37° C. for two days in darkness, then for two days in the light,
(c) at 27° C. for two days, (3) then exposing to ultraviolet light (250 nm) the white and vigorous strains derived from each culture effected on the selective media, for two hours at 4° C., (4) reinjecting the strains into "STARON" medium, (5) incubating the resulting cultures for two days at 37° C. plus two days at 27° C. after having removed, before the reduction in temperature from 37° to 27° C., the strains which are growing;

(6) cultivating said strains on the liquid and stirred "STARON" medium for two days at 27° C., (7) proceeding with sterile samplings, (8) mixing in the presence of acridine orange the most active strains rich in proteins, poor in glycosamine and antibiotics;

(9) incubating the resulting strains onto "STARON" medium for two days at 27° C., (10) proceeding with micro-isolations, and (11) incubating for two days the resulting strains at 27° C.; the strains thus obtained are subjected again to the cycle defined above, steps 1 to 11), for a sufficient number of cycles to obtain a strain possessing the desired characteristics.

It is also possible to make the strains undergo a partial cycle.

In fact, the troublesome criteria that it is desired to eliminate generally disappear one after the other; it is hence not necessary to maintain in the selection cycle this step aimed at eliminating said criterion. It is within the scope of the one skilled in the art to determine, by means of controls carried out in the course of each cycle, the steps to be maintained and those to be eliminated.

In the process according to the invention, applied to form Trichoderma Album, a batch of eleven culture media is utilized; eight media are constituted by an inorganic solution at pH=6.8 containing the following constituents:

$KH_2PO_4 = 1$ g; $MgSO_4, 7H_2O = 0.5$ g;
$KCl = 0.2$ g; $CaCl_2 = 0.2$ g;
$FeSO_4, 7H_2O = 0.03$ g; $ZnSO_4, 7H_2O = 0.01$ g;
$CuSO_4, 5H_2O = 2$ mg;
distilled water: amount sufficient for 100 ml;
gelose 20 g, to which the following components are added:

Medium 1): 30 g of glycerol + 2 g of urea
Medium (2): 20 g of saccharose + 3 g of allantoin
Medium (3): 20 g of starch + 5 g ammonium sulfate
Medium (4): 20 g of glucose + 7 g of tyrosine
Medium (5): 5 g apple pectin + 7 g anthranilic acid
Medium (6): 20 g of starch + 5 g of sodium nitrate
Medium (7): 10 g of mannitol + 8 g of lactic casein.
Medium (8): 20 g of gluconic acid + 10 g of gelatin.
Medium (9) is "STARON medium" containing glucose = 20g; peptone = 6 g; yeast extract = 1g; Corn Steep = 4g; NaCl = 0.5g; $MgSO_4$, 7 $H_2O = 0.5$ g; $KH_2PO_4 = 1$ g; $FeSO_4$, $7H_2O = 10$ mg; distilled water, amount sufficient for 1 l; gelose = 20 g for solid media.

Medium (10) is constituted by food potatoes and medium (11) is lactoserum at 40 g/l.

As previously indicated, it is possible to subject the cultures to partial cycles; for example in the case of Trichoderma Viride, it is possible to subject each culture effected on each of the 11 media to steps 1 to 4, then proceed with incubation for two days at 27° C., then with micro-isolations to select white and vigorous strains, and then to incubation, again for two days at 27° C., of these white and vigorous strains; the strains thus obtained are then inoculated onto eleven selective media and the partial or complete cycles are recommenced, the complete cycles including steps 1 to 11).

Figure 4:
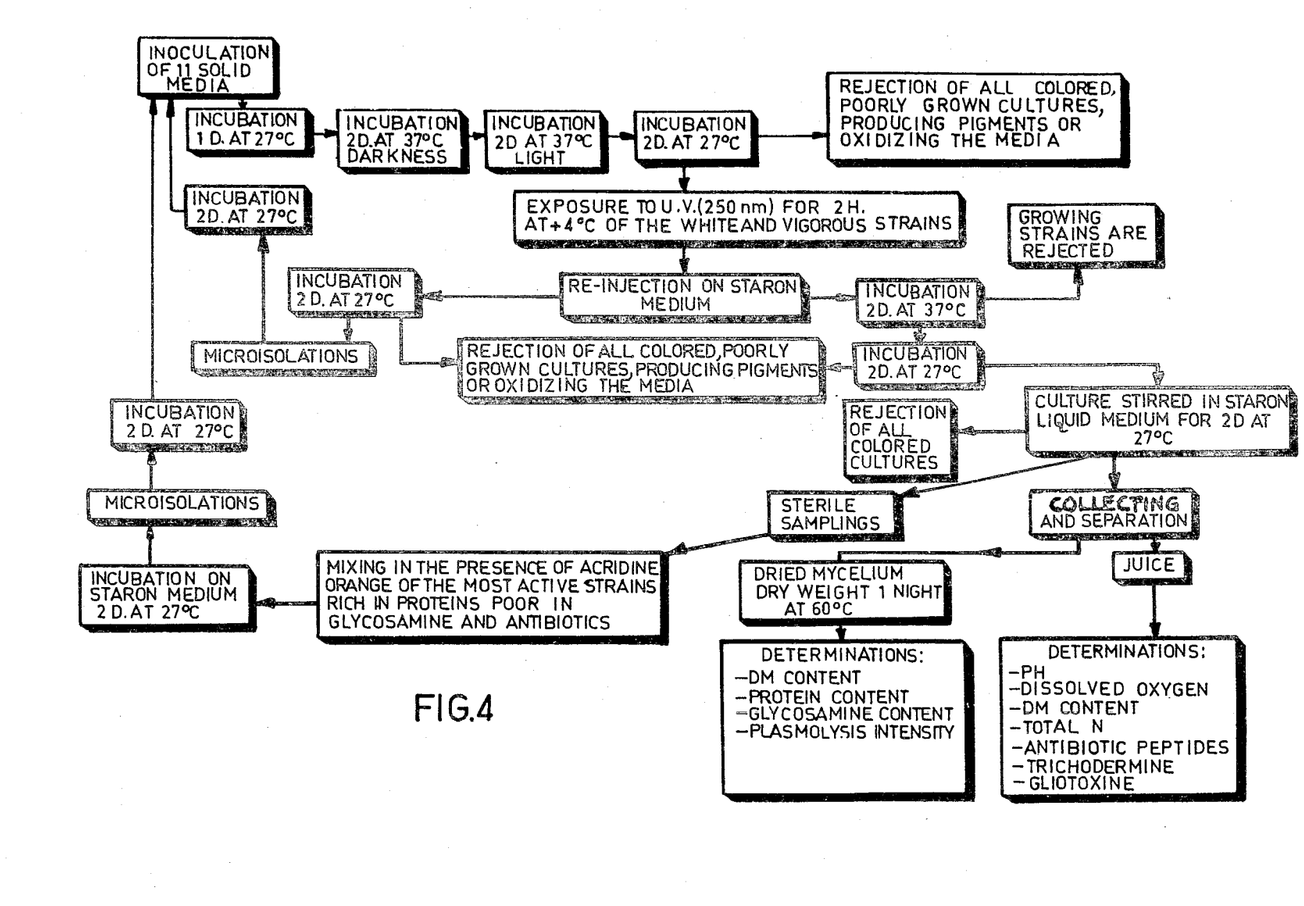
FIG. 4 shows diagrammatically the partial or complete cycles of the mutation process according to the present invention.

The partial or complete cycles of the process according to the present invention are shown diagrammatically in FIG. 4.

The control methods carried out throughout the cycles shown in FIG. 4 are notably;
- titration of the glycosamine after hydrolysis of the mycelium in 6 N HCl and resolution in an autoanalyser known under the tradename "Technicon $TSM_1$"
- microbiological titration of the antibiotic peptides, of the trichodermine and of the gliotoxin after extraction with n-butanol,
- measurement of the intensity of plasmolysis (drying at 60° C., grinding and determination of the water-soluble fraction at pH=8).
- the weight of the dry material produced and determination of its protein content by microkjeldahl.
- weight determination of the amount of dry matter consumed in the medium.

The incubations carried out at 27° C. according to the process of the invention are still carried out in natural light. When it is specified that the incubations are carried out at 37° C. in light, it is a white light of intensity 2 to 300 watts per square meter.

The microseparations carried out in the course of the process according to the present invention consist of separating the hyphae by means of an optical microscope.

The number of cycles to be carried out depend on the original strain and the desired characteristics. The control methods enable the determination of whether these characteristics are reached.

According to the process of selection of the present invention, it is possible to obtain novel strains possessing advantageous properties, exploitable in numerous fields, notably for the production of food biomasses.

The process has been notably applied with success to Trichoderma Viride, *Fusarium roseum,* Bauveria Tenella, *Thrichoderma polysporum, Aspergillus oryzae* and is illustrated by Examples V and VI below.

Other examples of the application of the process of selection have been mentioned previously.

DESCRIPTION OF PREFERRED EMBODIMENTS

The invention will now be described in more detail in the illustrative but non-limiting Examples which are given below:

EXAMPLE I

Cultivation in fermentation device

In this example, there are processed, according to the process of the invention, liquid culture media containing 60 or 90°/$_{oo}$ of dry matter (grams per volume) and derived respectively from lactoserum, from alfalfa juice, from wheat flours, protein effluents, potato juices, corn steep (maceration waters in starch factories from corn grain) and from beetroot molasses.

The fermentation apparatus according to the present invention is used. In the vat 1, are introduced 100 liters of medium and 10 l Trichoderma Album obtained by cultivation with a stirrer. During the three to five first hours of cultivation, the latter has been aerated by aeration means 3 which were constituted in the present case by a circular tubing provided with holes and with an air inlet device. The amount of air injected was such that the dissolved $O_2$ content was comprised between 6 and 10 mg/l. The temperature of the culture medium was kept between 24° and 28° C. and the pH at a value comprising 3.7 and 4.8 with an acid or a base.

When the mycelium has been in its exponential phase processing according to the operational method described above followed, that is to say the valve 10 was opened and the circulating pump 15 and the centrifuge 12 put into operation. The oxygen flow rate in the centrifuge was regulated so as to keep the dissolved oxygen content at a value comprised between 6 and 10 mg/l. After 15 to 20 hours of cultivation, the mycelium was collected by drawing off and it was filtered on a filter press; 7 to 9 kg of mycelium cake with 50% of dry matter was obtained. This cake was then dried on a "Hatmaker" type roller or by freeze-drying and a filamentous flour with 57–65% of protein was obtained. The precentage composition of the products obtained with each medium as well as their composition in amino acids was substantially the same as that given in Tables I and II. The amounts of dry matter, produced and remaining at the end of 10 and 20 hours, are recorded in Table IV.

EXAMPLE II

Cultivation with stirrer

Trichoderma Album was cultivated with a stirrer (150 rpm) in Erlenmeyer flasks of 500 ml containing 100 ml of medium. The media included, per liter, 40 to 70 g of dry matter adjusted to 3% of N; the starting pH was 4.5. The duration of the culture was from 20 h to 40 h at 27° C. The harvest of mycelium was effected on a filter press and the collecting of freeze-drying.

The averages of the results obtained are given in Table III below:

TABLE III

| Medium — starting pH = 4.5 | — starting dissolved $O_2$ = 8 mg/l | pH | | Dissolved $O_2$ mg/l | | Produced DM g/l | | Remaining DM g/l | |
|---|---|---|---|---|---|---|---|---|---|
| | | 20h | 40h | 20h | 40h | 20h | 40h | 20h | 40h |
| 40°/$_{oo}$ | DM | 6.5 | 7 | 4 | 4 | 6 | 9 | 30 | 27 |

TABLE III-continued

| Medium<br>— starting pH<br>= 4.5 | — starting dissolved $O_2$<br>= 8 mg/l | pH | | Dissolved $O_2$ mg/l | | Produced DM g/l | | Remaining DM g/l | |
|---|---|---|---|---|---|---|---|---|---|
| 70°/$_{oo}$ | DM | 6.5 | 6.2 | 5.0 | 2.0 | 12 | 18 | 49 | 41 |

DM = dry matter.

Under the above operational conditions, the optimization of the culture is not possible; nonetheless, the yields of mycelium are excellent, but the extraction of the media rarely exceeds 50% due to the fact of the rapid fall in dissolved oxygen and of the considerable variations in pH.

Other tests carried out according to the above operational method, but keeping the pH at a value between 3.7 and 4.8 and the dissolved oxygen content between 6 and 10 mg/l, have shown that under these conditions of pH and dissolved $O_2$, optimization could be obtained.

EXAMPLE III

Comparison of culture in a fermentation device according to the invention with respect to culture in a traditional fermentation device.

In this example, the culture of Trichoderma Album was carried out on the media defined in Example I under the operational conditions described in Example II; the culture media contain 60 and 90°/$_{oo}$ of dry matter; the pH was kept at 4.5 and the temperature at 27° C. The amounts of dry matter produced and remaining at the end of 10 h to 20 h of culture were measured. The results obtained are reported in Table IV below.

The results of Table IV show that all the cultures produced with the apparatus according to the invention were successfully carried out; the results obtained are very good. On the other hand, the cultures effected in the traditional manner, that is to say in a fermentation device adapted for obtaining bacteria, yeasts or to produce antibiotics, enzymes etc . . . , were only validly effected on two substrates, namely lactoserum and wheat flour.

In conclusion, the apparatus according to the invention enables the obtention of a higher biomass production and more extensive extraction of the media.

TABLE IV

| Pasteurized media<br>4% of N/DM<br>pH kept at 4.5<br>temperature 27° C. | | Dissolved $O_2$ mg/l | | DM Produced g/l | | DM Remaining g/l | |
|---|---|---|---|---|---|---|---|
| | | 10h | 20h | 10h | 20h | 10h | 20h |
| fermentation in a traditional fermentation device (wheat flour lactoserum) | 60°/$_{oo}$ DM | 5 | 3 | 15 | 19 | 33 | 20 |
| | 90°/$_{oo}$ DM | 4 | 1.5 | 21 | 25 | 50 | 30 |
| fermentation carried out with the apparatus according to the invention (7 substrates of Ex. I) | 60°/$_{oo}$ DM | 8 | 7 | 27 | 35 | 15 | 3 |
| | 90°/$_{oo}$ DM | 6 | 6 | 30 | 45 | 38 | 10 |

EXAMPLE IV

Nutritional value of Trichoderma Album mycelium

The nutritional value of Trichoderma Album mycelium obtained according to Example I, was compared with the nutritional value of lactic casein, of soya cake, of sesame cake, of Paris mushrooms and raw lupin seeds.

The CEP (weight gain/protein ingested) were determined on young starved male S P F rats of Sprague Dawley breed; the duration of the experiment was 17 days and the protein levels in the foods was 10%. Each diet was rebalanced with the limiting indispensable amino acids. Each experimental batch included twenty animals.

The composition of the diet and the results obtained are shown in Table V.

Analysis of the results of Table V show that the proteins of Trichoderma Album possessed a nutritional value equivalent to lactic casein supplemented with methionine and higher than cooked soya cake and sesame cake.

The low protein efficiency coefficient of raw lupin flour is due to antinutritional factors contained in this seed. As for the low nutritive value of the Paris mushroom, for the rat, it can doubtless be explained by the high content of carpophores in the cell walls. In fact, in that case, the consumption is high.

EXAMPLE V

Selection of Trichoderma Album strain

By the selection process according to the present invention, there was isolated, from Trichoderma Viride, the novel species Trichoderma Album which is applied in the process for producing proteins according to the present invention.

The species Trichoderma Album possesses little wall; it does not produce antibiotics nor diffusible pigments contrary to the species Trichoderma Viride from which it is derived. It does not possess colored and thermophile hyphae.

The Trichoderma genus belongs to the class of imperfect filamentous fungi (adelomycetes=hyphomycetes), to the Moniliales order and to the Moniliacae family.

The branched, partitioned, mycelium is white to light green in color. The conidia, generally green are isolated, round, monocellular; they are borne by the verticilliar conidiophores.

The Trichoderma are saprophytic organisms of soils. It is considered that they are beneficial, since they are frequently antagonistic to phytopathogenic fungi. They produce numerous enzymes and antibiotics.

This novel species has been obtained by the process of selection according to the invention.

After 1400 cycles (partial or complete) carried out according to the cycle shown in FIG. 4, an inoffensive, active polyphage strain of Trichoderma was obtained, whose mycelium possesses high nutritional value for animals.

The elimination of troublesome characteristics contained by the original strain and the extensive selection of performance and of food quality fully confirm the exceptional genetic potentialities possessed by the fungi.

The isolated Trichoderma Album species possesses, as appears clearly in Table VI below, high speed of multiplication and energy efficiency. This novel species possesses little cell walls, and a high heat plasmolysis index. In addition, it does not possess hyphae productive of antibiotic peptides, of gliotoxin, of trichodermine and of pigments; it does not include individuals thermophile with colored mycelium. Also, it forms a hybrid very poorly with its ancestor, which confirms that there was genetic restructuration.

In Table VI, the results of analysis carried out on cultures at the end of 100, 300, 1000 and 1400 cycles according to the process, as well as the results of analyses carried out on the original Trichoderma Viride strain, are indicated.

The Trichoderma Album strain can be preserved by planting out.

EXAMPLE VI

Application of the selection process according to the invention to the strains Fusarium roseum, Bauveria Tenella, Trichoderma polysporum, Aspergillus orizae.

The selection process for micro-organisms according to the invention is applicable to the improvement of other micro-organisms (fungi, yeasts, bacteria); it has permitted the selection of germs possessing well-defined specific properties. In each case, it suffices to make a sound choice of the selection criteria, the culture media, and to use adequate control techniques.

By this process, have been obtained:
a *Trichoderma polysporum* antagonist to phytopathogenic fungi,
a non-pathogenic systemic *Fusarium roseum* and leading to protection of plants against phytopathogenic fusariums,
*Aspergillus flavus* producing no aflatoxins,
a *Penicillium coconeum* producing goat's cheese aroma,
Streptomyces producing hybribes antibiotics,
bacteria and streptomyces producing endopeptidases,
*Acrostalagmus aphidum* hyperpathogenic to greenfly.

Table VII illustrates some of the results.

The results in Table VII show that from biological material of different origins, it is possible to achieve very varied and very precise objectives. The selection of interesting characteristics chosen and the removal of troublesome properties are more or less long according to the wild micro-organisms tried. Sometimes the obstacles are considerable, and it would be preferable to change the original strain to reach the set objective. In all cases, interesting results are obtained.

EXAMPLE VII

Enhancement of the value of soluble fish protein concentrates

A soluble fish protein concentrate was used which titrated 90% of proteins to dry material. This concentrate was dissolved in four volumes of water (weight/volume).

In the apparatus according to the invention 30 liters of the concentrate solution defined above was introduced and one to two liters of Trichoderma Album obtained by cultivation with stirring.

The temperature was kept at 24°-28° C. and the pH of the medium at a value comprised between 3.7 and 4.8.

Periodically, samples were taken to determine the bitterness of the soluble fish protein concentrate. The reaction was stopped when the concentrate was devoid of bitterness, that is to say after about three to five hours.

The product obtained was a mixture of concentrate and mycelium which it was possible if necessary to separate by filtration or centrifugation.

In the above laboratory trial there was used as a starting material a soluble fish protein concentrate which was dissolved in water to obtain a liquid nutrient medium. In practice it is possible to cause the Trichoderma Album to act directly after papain hydrolysis after separation of the insolubles. In this way a drying step is avoided and an unnecessary dissolving step.

EXAMPLE VIII

Purification of sugar diffusion juices

Diffusion juices, which are diffusion juices obtained from dry chicory roots crystallized with difficulty due to the fact of the presence of impurities, such as, for example, phenols and amino acids.

If one operates according to the process of the invention by using, as a nutrient medium, a diffusion juice, there is obtained on the one hand a clarified juice which crystallizes well and for this reason simplifies the subsequent sugar manufacturing technology and on the other hand Trichoderma Album proteins. In fact, the fungus applied consumes all the nitrogen present as impurity in this juice and the carbohydrates and the mycelium is obtained which has the properties defined in Table I.

For example if a diffusion juice is utilized titrating 17% of dry matter and containing 1% of N with respect to the dried material, it is possible to obtain on the one hand, a clarified juice titrating 15% of dry material and on the other hand, 15 to 20 g/l of diffusion juice with 50% of Trichoderma Album proteins.

Thus instead of obtaining molasses, which are sugar industry byproducts, according to the invention there is obtained a protein fraction titrating 50 to 65% of proteins and the crystallization of sugar is improved.

TABLE V

| Diets | Composition of diets in %; GMQ; CEP | | | | | | |
|---|---|---|---|---|---|---|---|
| | I | II | III | IV | V | VI | VII |
| Lactic casein | 12 | 0 | 0 | 0 | 0 | 0 | 0 |
| Cooked soya cake | 0 | 22 | 0 | 0 | 0 | 0 | 0 |
| Cooked Sesame cake | 0 | 0 | 20 | 0 | 0 | 0 | 0 |
| Raw "New Land" lupin flour | 0 | 0 | 0 | 28 | 0 | 0 | 0 |
| Paris mushrooms | 0 | 0 | 0 | 0 | 25 | 0 | 0 |
| Trichoderma Album dried on the "Hatmaker" | 0 | 0 | 0 | 0 | 0 | 20 | 0 |
| Freeze-dried Trichoderma Album | 0 | 0 | 0 | 0 | 0 | 0 | 18 |
| Cornstarch | 53.75 | 44.75 | 46.50 | 38.35 | 41.60 | 41.65 | 48.75 |
| Glucose | 20 | 20 | 20 | 20 | 20 | 20 | 20 |
| Peanut oil | 8 | 8 | 8 | 8 | 8 | 8 | 8 |
| Cellulose | 2 | 1 | 1 | 1 | 1 | 1 | 1 |
| Vitamin and mineral complement | 4 | 4 | 4 | 4 | 4 | 4 | 4 |
| DL methionine | 0.25 | 0.25 | 0 | 0.35 | 0.4 | 0.35 | 0.25 |
| L lysine, HCl | 0 | 0 | 0.5 | 0.20 | 0 | 0 | 0 |
| L threonine | 0 | 0 | 0 | 0.10 | 0 | 0 | 0 |
| Average starting weight of the rats (in g) | 52 | 51 | 51 | 51 | 51 | 51 | 51 |
| Average weight of the rats after 17 days (in g) | 129 | 111 | 119 | 70 | 85 | 132 | 131 |
| Ingested/J/al (in g) | 12.5 | 10.4 | 10.8 | 5.9 | 9.2 | 12 | 12 |
| G M Q | 4.5 | 3.5 | 4.0 | 1.1 | 2.0 | 4.8 | 4.7 |
| C E P | 3.7 | 2.9 | 3.0 | 1.7 | 2.0 | 3.7 | 3.6 |

TABLE VI

| | Wild Strain | 100 passages | 300 passages | 1000 passages | 1400 passages |
|---|---|---|---|---|---|
| Doubling time (in hours) | 6.00 | 5.00 | 3.50 | 2.30 | 1 to 2 |
| Energy efficiency (amount of DM necessary to obtain 1 g of dry mycelium) | 5.00 | 4.00 | 3.50 | 2.00 | 1.60 |
| Efficiency of the protein synthesis (amount of DM necesary to obtain 1 g of proteins) (in g) | 12.5 | 9 | 7.4 | 3.4 | 2.5 |
| Average proportion of protein material of the mycelium (in % DM) | 40 | 45 | 47 | 60 | 65 to 70 |
| Amount of proteins produced in 48 h from 40 g of DM | 1 | 1.5 | 2.7 | 7 | 10 |
| Plasmolysis index (fraction soluble in water at pH = 8 after 20 h of drying at 60 C (in %) | 10 | 20 | 40 | 55 | 60 to 70 |
| % of proteins in the plasmolysed fraction | 35 | 45 | 50 | 50 | 50 to 60 |
| Glycosamine (in % for 16 g of N) | 18 | 15 | 9.5 | 2.2 | 0.7 |
| Antibiotic peptides excreted (in g/l of culture medium) | 2-5 | 1-2 | 0.5 | 0 | 0 |
| Thermophile fragments (in °/oo) | 12 | 2 | 0.5 | 0 | 0 |
| Exhaustion degree of the media in 48 h for 40 g DM/l pH = 4; 27 C; 4 to 8 mg of dissolved oxygen/l (in % DM) | 20 to 25 | 35 | 50 | 60 to 70 | 70 to 75 |
| Proteic efficiency coefficient in the rat after 17 days of balanced diet including 10% of proteins | — | — | — | 3.7 | 3.9 |

TABLE VII

| | Wild Strains | 50 cycles | 200 cycles | 500 cycles | 1000 cycles |
|---|---|---|---|---|---|
| *TRICHODERMA POLYSPORUM* | | | | | |
| Protection of the bean against Colletothricum, Lindemuthianum Number of plantules protected in % | 5 | 60 | 95 | 98 | 98 |
| *ASPERGILLUS FLAVUS* | | | | | |
| mg of aflatoxins produced per liter of culture medium | 1200 | 25 | 0 | 0 | 0 |
| *FUSARIUM ROSEUM* | | | | | |
| Protection of peas against pathogenic fusariums Number of plantules protected in % | 0 | 15 | 25 | 55 | 70 |
| *STREPTOMYCES AUREUS* | | | | | |
| mg of endopeptidase produced per liter of culture medium | 5 | 200 | 1250 | 4300 | 6200 |
| *STREPTOMYCES GRISEUS* producer of nigericine | | Grisorixine | | | |
| mg of grisorixine and of nigericine produced per liter | 0 / 800 | 200 / 350 | 650 / 0 | 2300 / 0 | 2300 / 0 |

(Grisorixine values above, Nigericine values below in the last row)

The embodiments of the invention in which an exclusive property or privilege is claimed are defined as follows:

1. Process for producing food proteins, comprising the steps of: cultivating the fungus Trichoderma Album (I-032) in liquid nutrient media at a temperature below 28° C.; the pH of said media being kept at a value between about 3.7 and 4.8; the nitrogen content (atomic N) of said media being adjusted to a value of about 4 to 5%, with respect to the dry material; the dissolved oxygen content being from about 6 to 10 mg/l; said cultivation being carried out with stirring which does not cause lysis of the fungus; and under conditions such that foaming is avoided.

2. Process according to claim 1, wherein the temperature is comprised between 24° and 28° C.

3. Process according to claim 1, wherein the nutrient media is derived from agricultural products, agroalimentary industry rejects or from protein substrates to be enhanced in value.

4. Process according to claim 3, wherein the agricultural products are:
   (a) flours selected from the group consisting of wheat, rye, corn, barley, oats and peas;
   (b) tubers and roots selected from the group consisting of potatoes, Jerusalem artichokes, manioc, sweet potatoes, beetroots, beetroot molasses, beetroot pulp, carrots and swedes;
   (c) the pulps and teguments of fruits selected from the group consisting of bananas, pineapples, oranges and apples;
   (d) marcs; and
   (e) fibrous products selected from the group consisting of bagasse, straw and wood.

5. Process according to claim 3, wherein the agroalimentary industry rejects are: bird droppings; liqid manures; household wastes; residual waters; effluents from preserving plants, protein plants or distillery vinasses; corn steep; diffusion waters from sugar factories; or products derived from marine creatures selected from the group consisting of fish and crustacae.

6. Process according to claim 5, wherein the products derived from marine creatures are the press liquors and concentrates of soluble fish proteins.

7. Process according to claim 3, wherein the protein substrates are beetroot pulps or soluble fish protein concentrates.

* * * * *